US006200295B1

(12) United States Patent
Burchett et al.

(10) Patent No.: US 6,200,295 B1
(45) Date of Patent: *Mar. 13, 2001

(54) NURSING BOTTLE WITH MEDICATION DISPENSER

(75) Inventors: Mark T. Burchett; Lori W. Burchett, both of Western Springs, IL (US)

(73) Assignee: The Medicine Bottle Co, Inc., Hinsdale, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/174,983

(22) Filed: Oct. 19, 1998

Related U.S. Application Data

(63) Continuation of application No. 08/754,894, filed on Nov. 22, 1996, now Pat. No. 5,824,012, which is a continuation of application No. 08/528,191, filed on Sep. 14, 1995, now abandoned, which is a continuation-in-part of application No. 08/315,201, filed on Sep. 29, 1994, now Pat. No. 5,487,750, which is a continuation-in-part of application No. 08/061,698, filed on May 12, 1993, now Pat. No. 5,383,906.

(51) Int. Cl.[7] .................................................... A61M 5/315

(52) U.S. Cl. .......................... 604/218; 606/236; 604/181; 222/133

(58) Field of Search ............................... 604/236, 56, 82, 604/187, 191, 212, 218; 222/133; 215/1.1

(56) References Cited

U.S. PATENT DOCUMENTS

| | | | |
|---|---|---|---|
| 5,383,906 | * | 1/1995 | Burchett et al. . |
| 5,487,750 | * | 1/1996 | Burchett et al. . |
| 5,824,012 | * | 10/1998 | Burchett et al. . |

* cited by examiner

*Primary Examiner*—Glenn K. Dawson
*Assistant Examiner*—Catherine Serke
(74) *Attorney, Agent, or Firm*—Niro, Scavone, Haller & Niro

(57) ABSTRACT

An integrated nursing bottle and liquid medication dispensing apparatus enables precise and independent control of both the rate of administration of the medication, and the amount by which it is diluted before reaching the infant's mouth. A preferred embodiment utilizes a sleeve with a restricted tip for receiving a syringe that permits the optimal mixing of medicine and a diluting fluid in the nipple area of the bottle while minimizing the loss of fluid in the syringe tip, thus ensuring the easy and accurate administration of medicine dosages.

3 Claims, 9 Drawing Sheets

Fig. 1
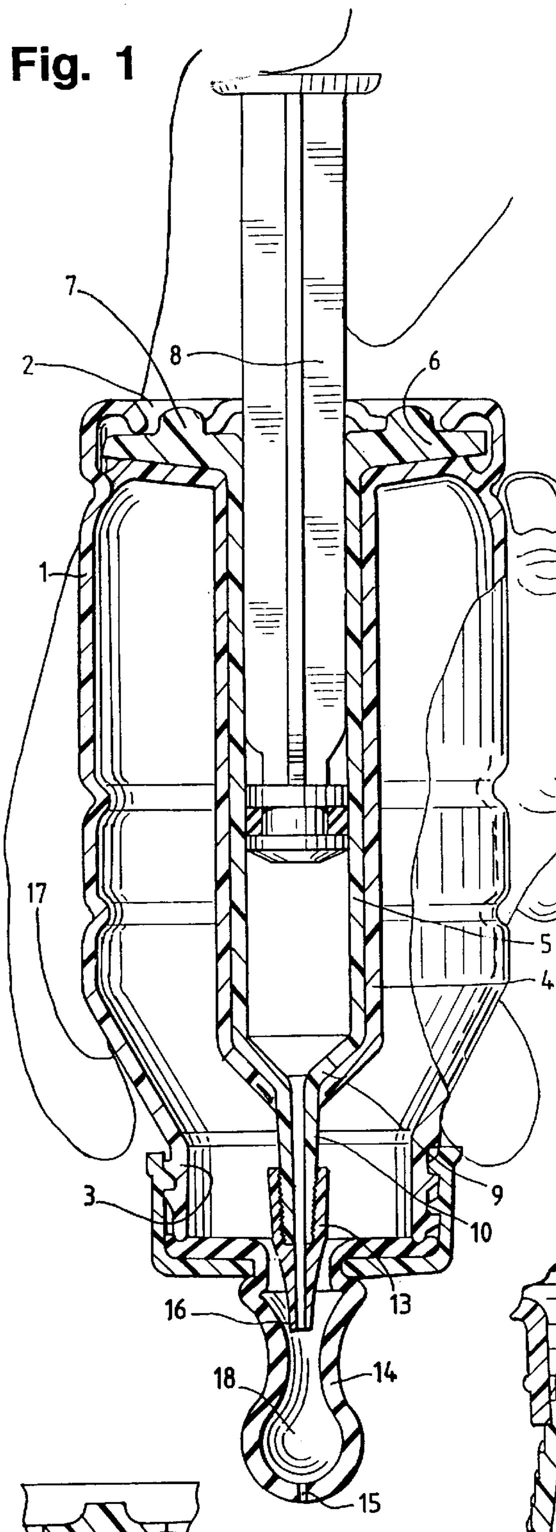
Fig. 3
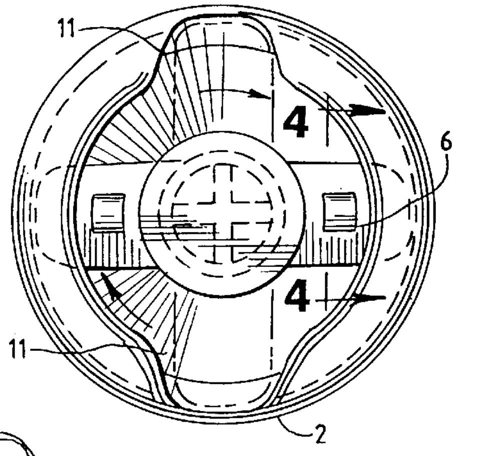
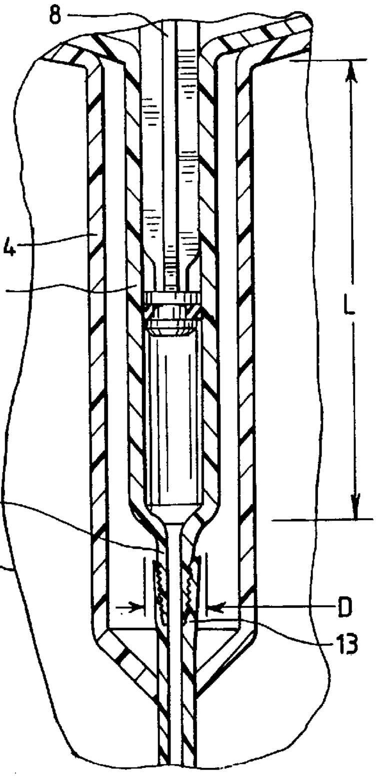
Fig. 2
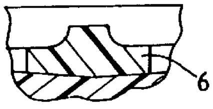
Fig. 4
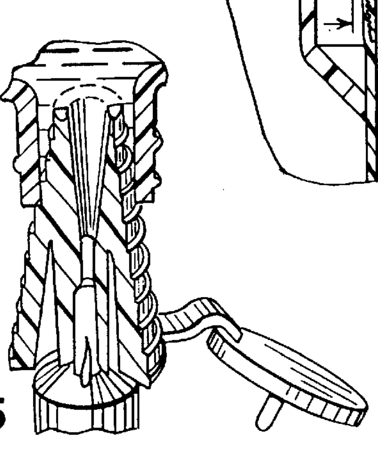
Fig. 5

Fig. 6
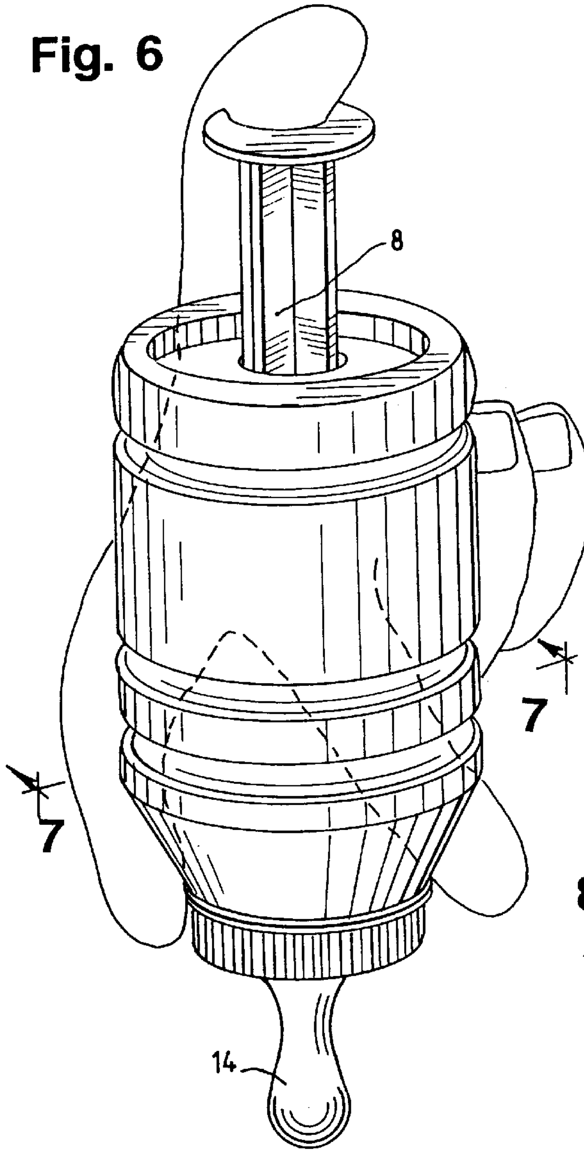
Fig. 7
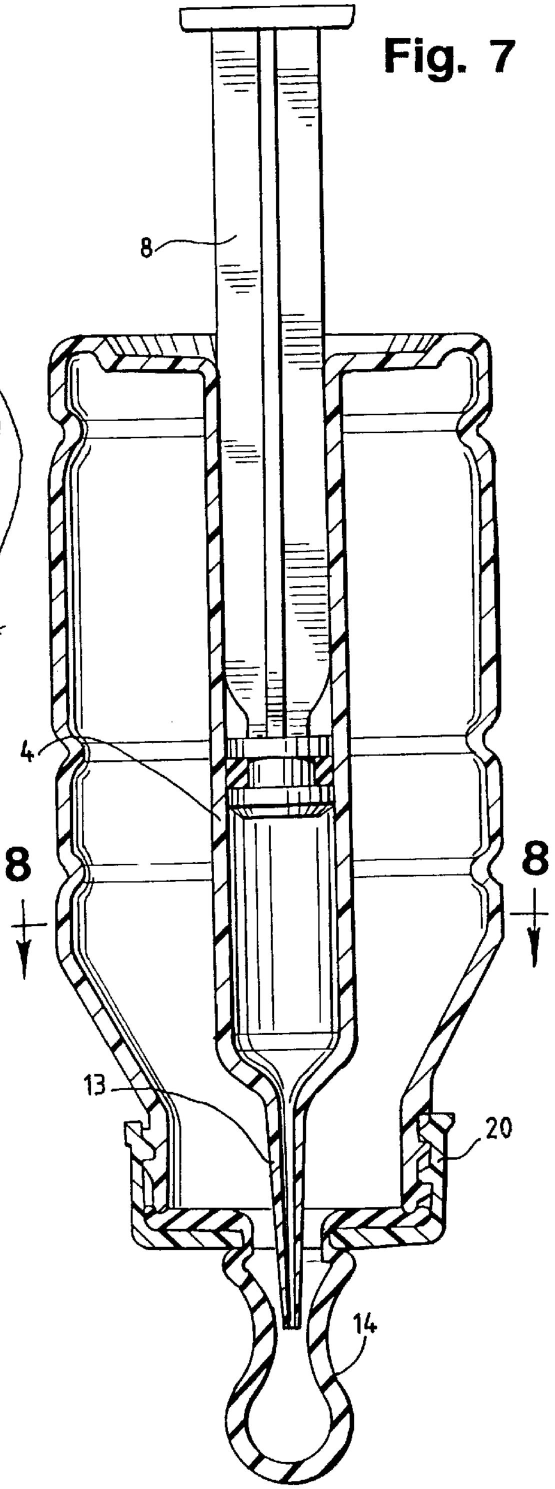
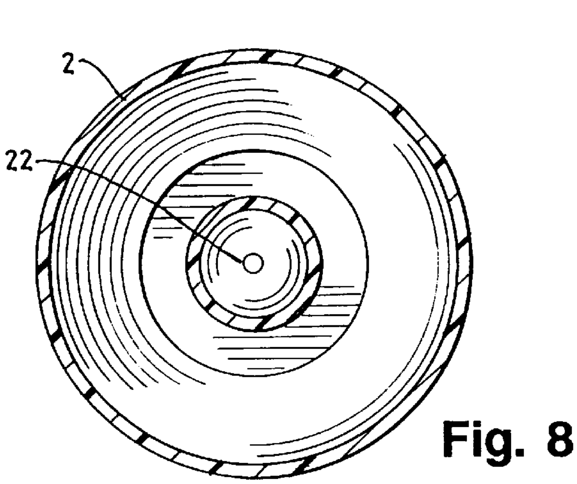
Fig. 8

Fig. 9
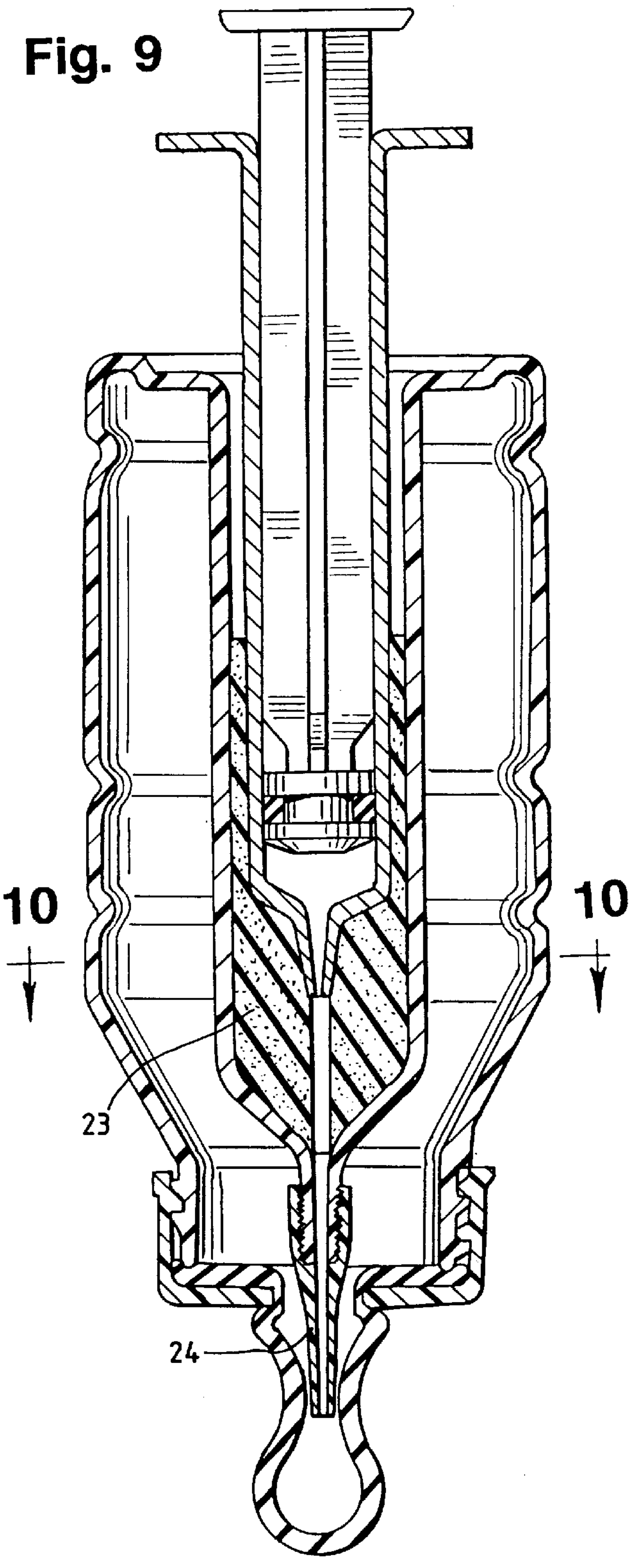
Fig. 10
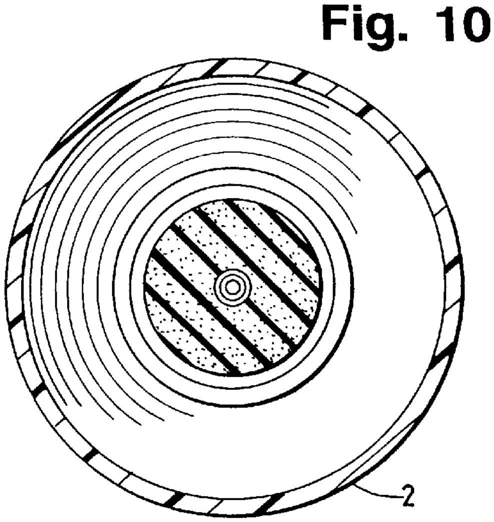
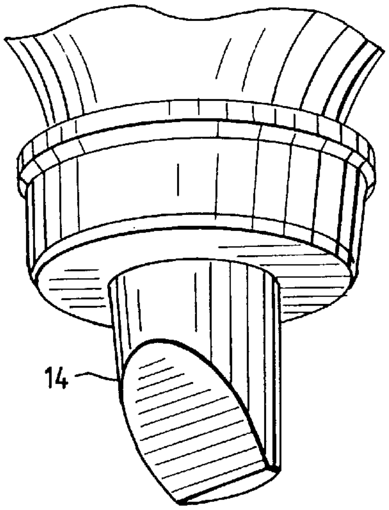
Fig. 11

Fig. 12
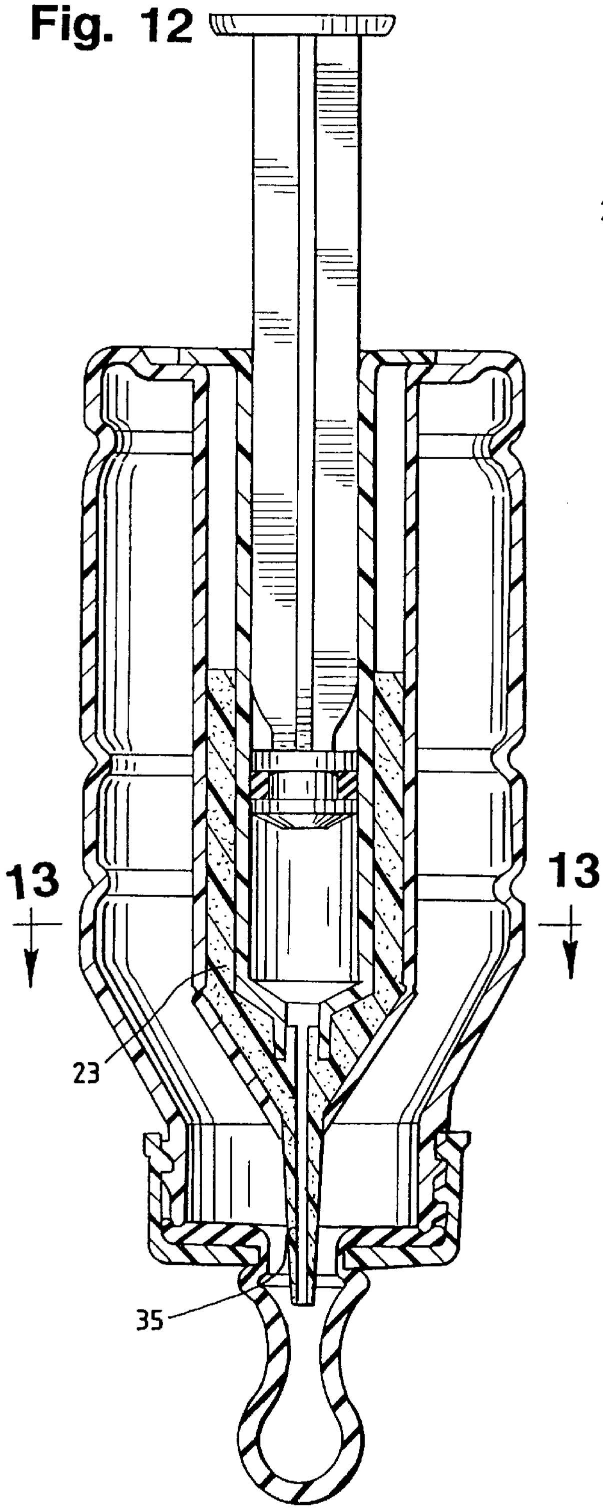
Fig. 13
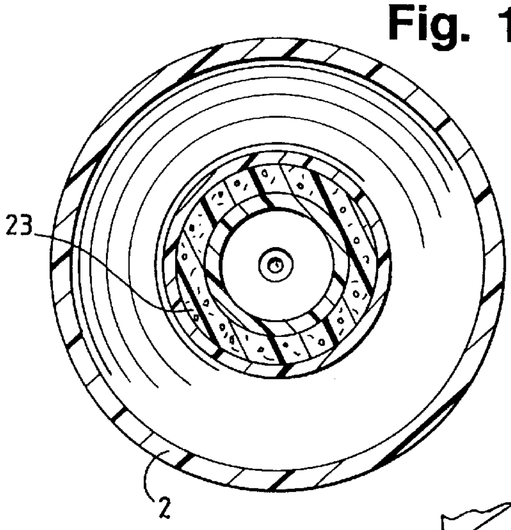
Fig. 14
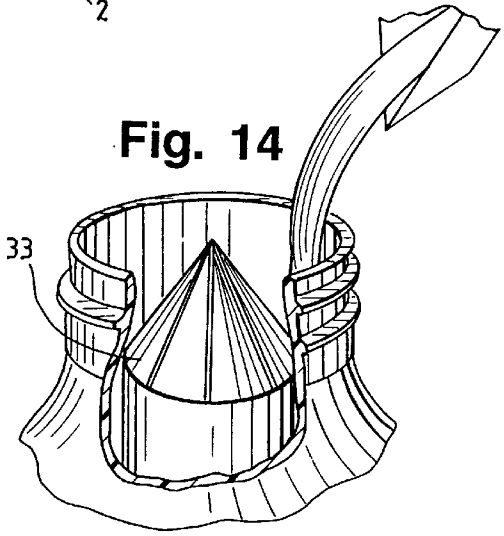
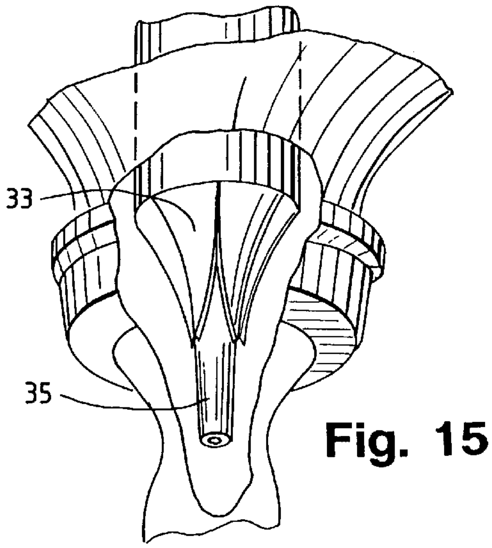
Fig. 15

Fig. 17
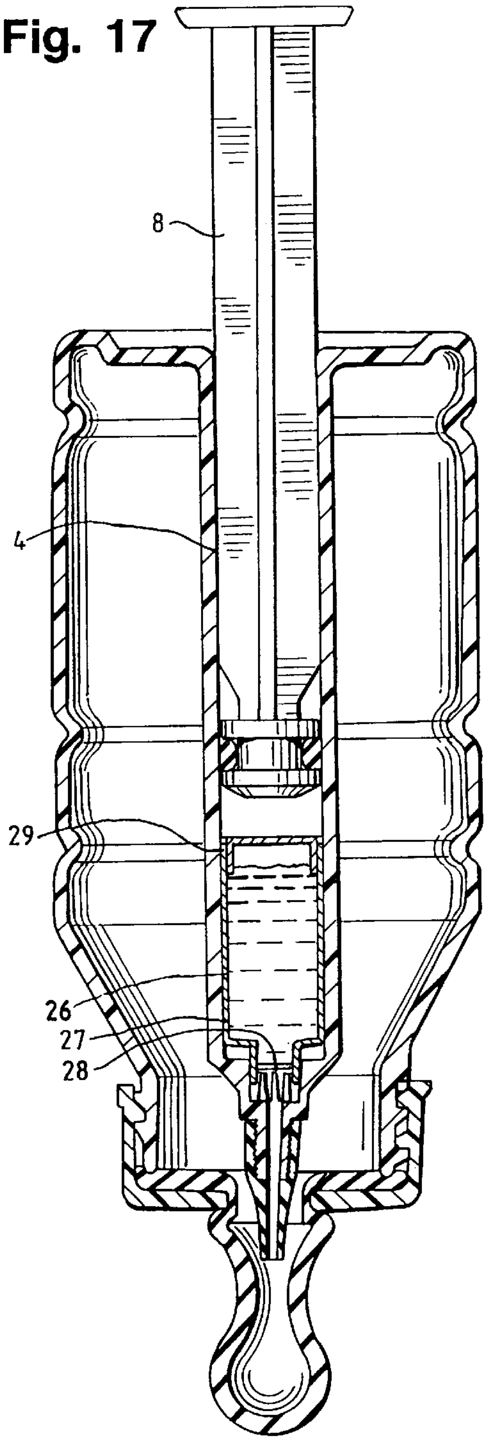
Fig. 18
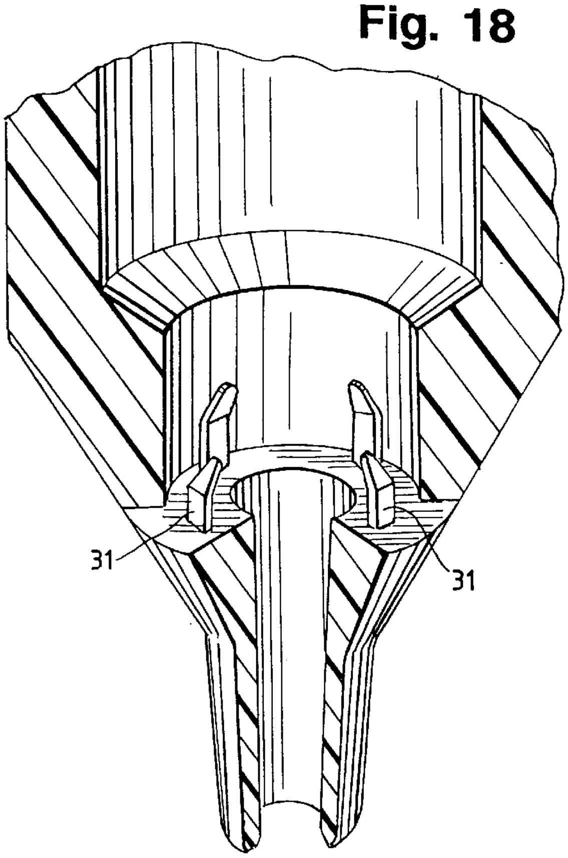
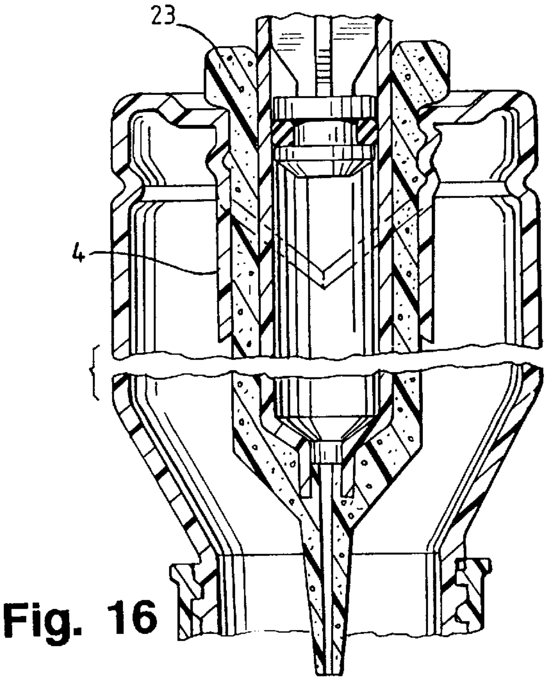
Fig. 16

NURSING BOTTLE WITH MEDICATION DISPENSER

This is a continuation of application Ser. No. 08/754,894, filed Nov. 22, 1996, now U.S. Pat. No. 5,824,012, entitled "Nursing bottle With Medication Dispenser," which is a continuation of U.S. patent application Ser. No. 08/528,191, filed Sep. 14, 1995, now abandoned, entitled "Nursing Bottle With Medication Dispenser", which is a continuation-in-part of U.S. patent application Ser. No. 08/315,201, filed Sep. 29, 1994, now U.S. Pat. No. 5,487,750, entitled "Nursing Bottle With Medication Dispenser," invented by Mr. Mark T. Burchett and Mrs. Lori W. Burchett, which is a continuation-in-part of U.S. patent application Ser. No. 08/061,698, filed May 12, 1993, now U.S. Pat. No. 5,383,906 entitled "Nursing Bottle With Medication Dispenser," invented by Mr. Mark T. Burchett and Mrs. Lori W. Burchett, of which such applications are incorporated by reference herein.

BACKGROUND OF THE INVENTION

1. Field of the Invention

Efforts to administer liquid medication to infants and young children often degenerate into contests of wills, with the infant enjoying all of the advantages. Unpalatable medication frequently ends up liberally distributed everywhere but in the infant's stomach. The struggle to insert a spoon, dropper or syringe into the infant's mouth actually risks injury to the baby's mouth and eyes. And, often the child swallows only an unknown portion of the liquid, leaving the dosage completely uncertain.

Repeated dosages become even more difficult, as the infant learns to recognize an unpleasant experience and becomes more adept at resisting it.

Our invention relates to a liquid medication dispenser that provides fully controllable, accurately metered mixing of liquid medication with palatable beverages such as milk, juice, infant formula, or any other pleasant-tasting liquid inside the nipple of a baby bottle. Both the amount of dilution and the speed of administration of the medication can be controlled independently of each other, in order to produce a mixture that remains palatable. The user is able to instantly adjust the flow of medicine in response to the child's reactions. The familiar shape of the baby bottle, and the ability to start feeding before the admixture of medication begins, soothes the infant into accepting the mixture with little or no protest. The liquid medication dispenser is graduated, enabling precise determination of the amount of medication administered.

Embodiments of our invention include an inexpensive device featuring an integral, graduated syringe; a disposable version intended for high-volume users such as hospitals or clinics; and a design intended for use with pre-packaged, pre-measured doses of liquid medication. Our preferred embodiment is a reusable device in which separate, graduated syringes are used in order to facilitate filling and/or heating the juice, milk or infant formula, while improving the ease and accuracy of loading a syringe with medicine.

2. Description of the Prior Art

Commercially-available devices for administering liquid medication to infants are limited to spoons and to plastic droppers or syringes not capable of use with baby bottles. See, for example, U.S. Pat. No. 4,493,348 (Lemmons), which describes such a plastic syringe and a device for filling it. The infant is presented with an evil-tasting medicine full strength, administered from an unfamiliar source.

Most children rapidly learn that the most satisfying response is to spit out the offending liquid.

Dilution of the liquid medication in milk is not a satisfactory solution. In the case of extremely unpalatable medications, the taste of the milk may become unacceptable. And, if the infant does not finish drinking, the problems of determining how much medicine has been administered, and completing the prescribed dosage, can become acute.

Several references disclose medication dispensers that mimic the familiar shapes of baby bottles or pacifiers, but that still provide the liquid medication full strength. See, for example, U.S. Pat. Nos. 5,176,705 (Noble); 5,078,734 (Noble); 5,129,532 (Martin); and 3,426,755 (Clegg). Other references disclose dispensers tipped with nipples. See U.S. Pat. Nos. 3,077,279 (Mitchell) and 3,645,413 (Mitchell). An insert for a baby bottle also has been proposed; the insert would convert a baby bottle into a liquid medication dispenser by fitting a vial into the bottle. See U.S. Pat. No. 5,029,701 (Roth, et al.). But, dilution of the medication with milk would be impossible in the Roth device; the infant would receive undiluted medication from the nipple—a practice that may make it difficult even to bottle-feed the infant later (because of the child's memory of the unpleasant taste), and that does nothing to alleviate problems with palatability of the medication.

Another reference, U.S. Pat. No. 5,244,122 (Botts), discloses a apparatus having two separate openings for different fluids that extend into the tip of the baby bottle nipple. Thus, botts, unlike the present invention, does not teach a device in which medicine and milk or other diluting fluid is mixed in the nipple area. Botts, further, unlike the present invention, teaches a device in which the medication is not controllable by the person administering the medication. The child sucks the medicine in from the very start and then when the medicine is gone, the child sucks air directly. When the nipple assembly is used with a syringe, the child will be able to suck directly on the nipple tube, drawing some medicine out and thus taking some control away from the operator.

Still another reference, U.S. Pat. No. 3,682,344 (Lopez), discloses a small, flexible enclosure on the exterior of the nipple itself, which is said to be suitable for dispensing medication or flavoring agents. Lopez' design, however, does not provide any dilution nor allow control of the rate of dosage. And, there is no method for measuring the amount of medication dispensed.

U.S. Pat. No. 2,680,441 (Krammer) discloses a baby bottle with a medicine dropper attached to its exterior; a small tube leads from the dropper through the exterior of the nipple itself, to one of a plurality of perforations in the tip of the nipple. Therefore, the liquid medication is not diluted before entering the infant's mouth. As a result, there is little improvement in palatability. Also, there is the chance of medicine being left over in the tube, thus contributing to greater inaccuracy in the dosage delivered. Further, the design does not allow the use of the nipple or sipper top to which the child is normally accustomed. And, the attachment of the dropper to the exterior of the bottle changes the appearance of the bottle and would make it quite difficult to operate the dropper and to hold the bottle with one hand, while soothing or cradling the infant with the other.

Still another reference, U.S. Pat. No. 4,821,895 (Roskilly), describes an attachment that replaces the cap and nipple of an ordinary baby bottle. The attachment comprises a threaded cap that sets the nipple off-center from the axis of the bottle; a mixing chamber below the nipple and communicating directly with it; a restricted passageway leading from the interior of the bottle to the mixing chamber, and a syringe assembly (also communicating with the mixing chamber) that projects sideways from the threaded cap at an angle of about 45° to the axis of the bottle. (See Roskilly's FIG. 2). In another embodiment (FIG. 3), Roskilly suggests a syringe assembly that projects at a 90° angle to the bottle axis, and that feeds medication downward into the bottle in a direction away from the nipple.

Neither of Roskilly's embodiments allows for controlled dilution of the medication, together with the ability to further dilute medication already injected should the taste become unpalatable. And, neither would be suitable for one-hand operation. Both involve large, axially-projecting syringes which present hazards for the infant's mouth and eyes during operation.

In short, until we made our invention there was no device suitable for one-handed operation for administering liquid medication to infants in admixture with juice, milk or formula at a controlled rate and dilution, while providing accurate measurement of the amount of medication administered.

SUMMARY OF THE INVENTION

Our invention provides an integrated feeding bottle and liquid medication dispensing apparatus that enables precise and independent control of both the rate of administration of the medication, and the amount by which it is diluted before reaching the infant's mouth. In our preferred embodiment, the bottle can be filled with milk or any palatable beverage and heated, if necessary, before the appropriate sized syringe containing the liquid medication is inserted into the coaxial sleeve in preparation for use. The different sized syringes which can be used with the bottle allow for a more accurate measurement of the dosage to be delivered.

One object of our invention is to provide an apparatus suitable for one-handed operation of varying grips which can be used to dilute and administer liquid medication to infants during drinking.

Another object of our invention is to provide a device which precisely meters the amount of liquid medication remaining to be administered.

A further object of the preferred embodiment of our invention is to provide a bottle which can be filled with milk, infant formula or other suitable diluent liquid before the appropriate syringe containing liquid medication is inserted.

An object of one alternate embodiment of our invention is to provide a disposable feeding bottle which can accommodate a range of standard-size syringes for liquid medication by means of an internal soft bushing that holds the syringe in place.

An object of another embodiment of our invention is to provide a device suitable for use with pre-packaged, pre-measured dosages of liquid medication that is suitable for one-handed operation and that can be used to dilute and administer liquid medication to infants during drinking or feeding.

BRIEF DESCRIPTION OF THE DRAWINGS

FIG. 1 shows the preferred embodiment of our invention, in a cross-sectional view along the longitudinal axis of the bottle.

FIG. 2 shows a cross-sectional detail of the variable-length and variable diameter internal injection tube.

FIG. 3 shows the syringe locking mechanism in unlocked position.

FIG. 4 shows a detail of the syringe locking mechanism.

FIG. 5 shows a Korc® funnel, which may be used to fill the syringe of the preferred embodiment from a bottle of liquid medication.

FIG. 6 shows the one-handed operation of a simplified embodiment of our invention using a built-in, nonremovable syringe.

FIG. 7 is a cross-sectional view of a simplified embodiment of our invention using a built-in, non-removable syringe.

FIG. 8 shows an end view of the bottom end of the disposable embodiment of our invention.

FIG. 9 is a cross-sectional view of a disposable embodiment of our invention suitable for use with a range of standard, off-the-shelf syringes.

FIG. 10 illustrates a detail of the disposable embodiment of our invention suitable for use with a range of standard off-the-shelf syringes.

FIG. 11 illustrates an alternative nipple or "sipper" top for use with our invention for older children.

FIG. 12 shows an example of a second disposable embodiment of our invention suitable for use with a range of standard, off-the-shelf syringes.

FIG. 13 illustrates a detail of the bushing used in our second disposable embodiment.

FIG. 14 shows the break-away portion of the second disposable embodiment preventing liquid from entering the internal sleeve.

FIG. 15 shows an exposed view of the bushing acting upon the break-away portion and the second disposable embodiment of our invention.

FIG. 16 shows the second disposable embodiment equipped with a shorter length internal sleeve and a full length, threaded bushing.

FIG. 17 shows another, alternate embodiment suitable for use with pre-packaged, pre-measured dosages of liquid medication.

FIG. 18 illustrates the operation of a seal-puncturing device suitable for use with pre-packaged, pre-measured dosages of liquid medication.

DETAILED DESCRIPTION OF THE PREFERRED EMBODIMENT OF FIGS. 1–6

Figure 19:
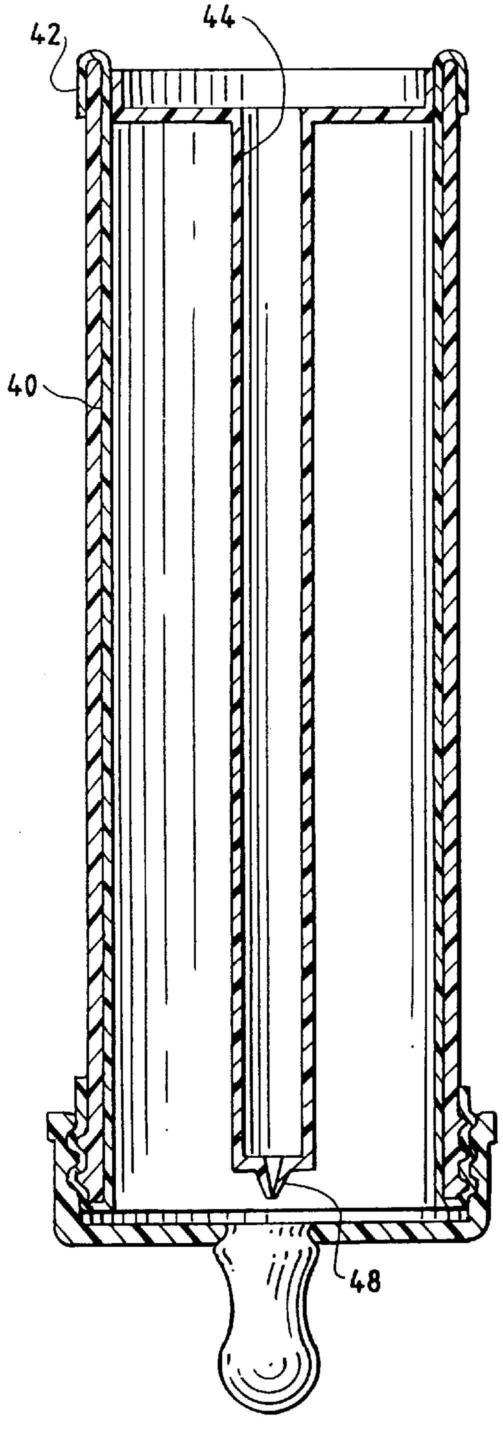
FIG. 19 illustrates an exposed cross section of another preferred embodiment of the present invention suitable for use with a deformable, prepackaged formula bag having a syringe sleeve.

FIG. 1 shows the preferred embodiment of our invention, which comprises a bottle 1 having a bottom end 2, a threaded top opening 3 and a coaxial, cylindrical internal sleeve 4. The internal sleeve 4 is sized to accommodate different sized removable, cylindrical syringes 5.

The syringe contains a plunger 8 of standard construction, which in this embodiment is marked with volumetric graduations which indicate the amount of liquid medicine remaining in the syringe 5 at any one moment. This also enables determination of the exact dose which has been administered to the infant at any one time. The top or distal end of the syringe possesses a coaxial, elongated hollow tip 9 which fits snugly into a corresponding hollow, elongated top 10 on the distal end of the internal sleeve 4, creating a liquid seal between the exterior of the syringe tip 9 and the interior of the sleeve tip 10.

The plunger end of the syringe 5 is fitted with a pair of locking wings 6 (shown in FIGS. 3 and 4). The syringe also has a ridged grip portion 7 which facilitates rotation about the longitudinal axis. Before operation, the syringe 5 is inserted into the sleeve 4 from the bottom end of the bottle. The locking wings 6 fit into the tapered opening 11 on the bottom of the bottle. (See FIG. 3). Using the ridged grip portion 7, the syringe is then rotated about 90° to the approximate position shown in FIG. 4. In that position, the locking wings 6 fit into tapered retaining slots 12 on the bottom of the bottle. The progressive taper on the retaining slots 12 engage the locking wings 6 and forces the syringe longitudinally upward inside the internal sleeve 4, creating a pressure seal between syringe tip 10 and sleeve tip 9.

The exterior of the hollow, elongated tip 10 of the internal sleeve is fitted with male threads. The male threads engage female threads of various sized screw-on tip members 13. One of the purposes of various sized tips 13 is to reduce the internal diameter and thus increase the pressure on the medicine being delivered up into nipple 14 in a controllable stream, near the perforation or perforations 15 through which milk passes during drinking. Different sized syringes need different sized tips to achieve optimum results. The nipple 14 is interchangeable with a sipper top for use by older children. For example, in a 5 ml. syringe, the tip member 13 has a distal end 16 with an internal diameter of approximately 0.030 inches. We have found that the preferred range of tip diameters is approximately 0.0625 to 0.010 inches. The use of a smaller internal diameter tip member 13 produces a more forceful jet of liquid medication in the direction of the perforations 15, which minimizes dilution. Thus, the level of dilution can be controlled by substituting tip members having differing internal diameters.

Additionally, by varying the length of tip member 13, the distance from the tip of the nipple at perforations 15 and the distal end 16 of the tip member 13 can be varied. This also allows control of the amount of dilution of the liquid medication: the closer the distal end 16 of tip member 13 is to the perforations 15, the more concentrated the medication will be as it enters the infant's mouth. Experience with particular children and with specific medication allows adjustment of that distance to provide the most effective amount of dilution. Typically, a distance of approximately ⅞ inch from the nipple provides a suitable starting point, as it is out of the biting or sucking area of the nipple 14; it is preferred to provide a capability for adjusting the separation distance from 1/16 inch to 1¼ inches. With practice, the amount of dilution (and therefore, the palatability of the mixture) can be controlled by varying the force exerted on plunger 8, as well as by changing the internal diameter of the tip member 13 and its distance from the perforations 15.

Alternatively, a series of semi-rigid plastic tubes 13 of varying lengths and internal diameters can be substituted for threaded tip members 13. In that instance, adjustment of length and/or internal diameter is accomplished merely by sliding the appropriate sized semi-rigid tube longitudinally over the elongated sleeve tip 10, thus achieving the optimal internal diameter and desired separation from the perforations 15. The tubes of varying lengths and internal diameters are retained by friction.

The apparatus is designed for convenient, one-handed operation. The coaxial location of the syringe 9 on the longitudinal axis of bottle 1 enables one to grip the bottle by means of tapered, ridged surface 17 and operate the plunger 8 with one finger. In operation, the child is first allowed to begin nursing, and to become accustomed to the familiar taste of milk, juice, or formula. After the child is comfortable, the rate of administration of medication and the level of dilution is controlled by depressing plunger 8 of syringe 5, forcing the liquid medication out through elongated syringe tip 9 and elongated internal sleeve tip 13, to mix with the milk, infant formula, or other palatable beverage in the interior of nipple 14 near perforations 15. If the infant notices the taste of the medication, it is a simple matter to stop administering the medication and allow the child to become accustomed once again to the taste of the beverage. In extreme cases, because of the open communication through annular space 18 between the interior of nipple 14 and the interior of bottle 1, residual medication remaining in nipple 14 can be fully diluted with the remaining beverage simply by shaking the bottle, thus encouraging the child to continue feeding almost immediately with minimal upset and avoiding any significant loss of liquid medication.

With experience, it is possible to determine the best combination of medication rate and tip characteristics which provides full discharge of medication with little or no need to dilute medication throughout the milk or other fluid by shaking the bottle. We have found that using a suitably restricted outlet hole diameter (preferably about 0.030 inches for a 5 ml syringe) usually enables the length of the tip extension member to be short enough to avoid protruding into the part of the nipple that the infant bites upon, thus going completely unnoticed by the child. This helps prevent collapse of the tip extension member and/or puncturing of the nipple, and a feature of the preferred embodiment.

Syringe 5 can be filled with liquid medication from a bottle using known techniques, such as the Korc® funnel illustrated in FIG. 5 or the BAXA™ top After filling, syringe 5 (with plunger 8 extended) is inserted into internal sleeve 4 and locked in place by means of locking wing 6, as explained above. The bottle 1 can be filled with juice, milk or infant formula and heated, if necessary; the nipple 14 can be attached using threaded cap 20, before the insertion of the syringe.

DESCRIPTION OF THE INEXPENSIVE EMBODIMENT OF FIGS. 7–8

FIG. 7 shows an alternative, inexpensive embodiment which does not require the use of separate detachable syringes. In the embodiment of FIG. 7, the coaxial, cylindrical internal sleeve 4 itself forms the barrel of the syringe, in which plunger 8 moves. The hollow elongated tip 9 of internal sleeve 4 in this embodiment connects directly to one of the threaded tip members or slip-on tip extension tubes 13. Because no separate syringe is used, the bayonet mounting assembly shown in FIGS. 3–5 of the preferred embodiment is unnecessary. Volumetric graduations 19 are engraved or otherwise marked directly on the exterior surface of internal sleeve 4, as well as on the plunger 8.

Because no separate syringe is used, it is necessary to fill the internal sleeve 4 with liquid medication before filling the bottle with juice, milk or infant formula. Internal sleeve 4 can be filled by fully withdrawing plunger 8, capping the tip member 13 and then pouring the liquid medication into internal sleeve 4 through the large hole 22 in the bottom end of bottle 1. Alternatively, with plunger 8 in the fully depressed position, and with nipple 14 and threaded cap 20 removed, the bottle assembly 1, including tip member 13, can be filled from a bottle of liquid medication using a Korc® funnel or similar device just as in the case of a separate syringe. In order to accomplish this, the diameter of hole 21 on tip member 13 should be approximately 0.030 inches to 0.0625 inches.

After the internal sleeve 4 has been filled with liquid medication, and apparatus has been filled with milk or other suitable liquid, the operation of the device is substantially the same as that of the preferred embodiment. Alternatively, a fixed, permanent tip member could be used with the syringe 5 to facilitate easier assembly. However, this feature would reduce the adjustability and control of medicine delivery.

DESCRIPTION OF DISPOSABLE EMBODIMENT OF FIGS. 9 AND 10

The disposable, single use embodiment of FIG. 9 is generally similar in configuration to the inexpensive embodiment of FIG. 7. It differs in that the coaxial cylindrical internal sleeve 4, which may be somewhat off center to accommodate certain existing standard syringes (e.g. the BAXA™ 10 ml. oral syringe), is sized slightly larger in diameter than standard, commercially available syringes. The disposable device is provided with one or more soft rubber or flexible plastic bushings 23, which fit inside internal sleeve 4. The bushings 23 are sized to accommodate specific, commercially available syringes which are held in place by friction. The tightness of bushing 23 provides a fluid seal between syringe 5 and tip 24. In this disposable embodiment, tip 24 is formed integrally with internal sleeve 23 and is of a fixed length and internal diameter, to provide an appropriate clearance between its distal end 25 and the perforations 15 in nipple 14. The lengths and hole diameters for tip 24 are generally similar to those set forth above for tip member 13 of the embodiment of FIGS. 1–4. Alternatively, this embodiment, like the others, can be used with a “sipper” top as shown in FIG. 11, in place of a nipple.

As in the case of the preferred embodiment, syringe 5 can be separately filled with liquid medication using a Korc® funnel or similar device. Bottle 1 can be filled with milk or other suitable formula and heated before insertion of the syringe, Operation of the disposable device is similar to that of the preferred embodiment, except that the clearance between the distal end 25 of the hollow tip extension 24 and the perforations 15 in the nipple 14 cannot be adjusted. It is necessary, therefore, to control dilution by solely varying the rate of injection of liquid medication. Various sized tips 13 could replace the fixed tip, if necessary to accommodate liquid medication of varying viscosity.

Alternatively, different bottles 1 could be manufactured to specifically accommodate a particular syringe 5. They would have an exterior dimension and interior sleeve 4 and specific tip member 13 of optimal, internal diameter and length to best accommodate one specific syringe.

DESCRIPTION OF THE ALTERNATE DISPOSABLE EMBODIMENT OF FIGS. 12–16 USING A BUSHING WITH AN INTEGRAL TIP EXTENSION MEMBER

In an alternate, disposable embodiment illustrated in FIGS. 12–16, a hollow projection on distal end of bushing 23 which obviates the need for a tip member 13. In this alternative embodiment, the bottle 1 incorporates an internal sleeve capable of receiving all syringes presently in common use.

As shown in FIG. 12, each of these syringes 5 is accommodated and held in place by means of a bushing 23 which is specific for that syringe and would incorporate specific tip characteristics, including the optimal internal diameter and length. The internal sleeve 4 has no tip, only a fold-out portion 33 through which the bushing tip protrudes, as shown in FIG. 15. The bushing could be held in place by either friction or alternatively by an interlocking means such as a screw threading mechanism. The purpose of the fold-out portion 33 is to prevent juice, milk or formula from entering the internal sleeve when filling the bottle, as shown in FIG. 14.

FIG. 13 shows the bushing 23. The bushing 23 interacts with the distal end of the syringe 5, so as to align the bushing tip 35 with the opening in the distal end of the syringe. The bushing itself provides the fluid passageway communicating from the syringe to the interior of the nipple. The dimensions and lengths of the bushing tip 35 are preferably similar to the size shown for the tip member in the embodiment of FIGS. 1–4. Thus, the control features in administering juice, milk or formula could be maintained without the need of an additional, separate tip member.

Alternatively, the internal sleeve 4 can be shortened to terminate 1 to 2 inches below the bottom of the bottle, as shown in FIG. 16. This sleeve 4 would accept a longer bushing 23 that specifically accommodates a particular size syringe. In this embodiment, the bushing 23 would perform the structural support normally performed by the sleeve 4. This bushing 23 would be held fast at the bottom of the bottle by threads or friction.

DESCRIPTION OF THE ALTERNATE EMBODIMENT OF FIGS. 17–18 USING PREPACKAGED DOSAGES OF LIQUID MEDICATION

The embodiment of FIGS. 17–18 eliminates the necessity for filling a separate syringe. This embodiment makes use of prepackaged plastic or paper cylindrical pouches of liquid medication containing premeasured dosages. FIG. 17 illustrates the placement of such a medication pouch 26 in the internal sleeve 4. The pouch 26 comprises a sealed, cylindrical package having an extension 27 of smaller diameter than the body of the pouch itself. Plunger 8 and/or pouch 26 optionally may be engraved or otherwise marked with graduations 19 showing the amount of liquid remaining. Cylindrical extension 27 is fitted with small diaphragm 28 near its distal end. The proximal end of pouch 26 is also fitted with a large diaphragm 29, having the same diameter as the pouch itself. Immediately proximal of diaphragm 29, one or more small air holes 30 are situated.

FIG. 17 shows that the coaxial, cylindrical internal sleeve 4 is fitted at its distal end with one or more projections 31, which are shown in detail in FIG. 18, that face away from the distal end of internal sleeve 4 and toward its proximal end, and the hole 22 at the bottom of bottle 1. The purpose of projections 31 is to pierce small diaphragm 28 when pouch 26 is depressed against the distal end of internal sleeve 4. The pouch 26 is held in place by friction. Alternatively, a puncture sleeve 33, used to pierce the small diaphragm 28, could slide inside the internal sleeve 4 prior to placing the pouch 26 in the internal sleeve 4. Thus, the puncture sleeve 33 is a removable feature performing the same function as the projections 31.

In operation, removable plunger 8 is depressed and its gasket 32 contacts a large diaphragm 29, thus forcing liquid medication out the distal end 25 of tip 24 into the interior of nipple 14. The purpose of air holes 30 is to relieve air pressure generated by gasket 32 as it descends to large diaphragm 29. Thus, this embodiment keeps the plunger 8 and its gasket 32 from making contact with any medicine.

Alternatively, the large diaphragm 29 contains perforations to release air pressure when it is seated above the pouch 26. The perforations are then sealed. The plunger 8 has perforations in its gasket 32 to allow the release of air pressure when sliding down into place above the large diaphragm 29. This control of air pressure in the internal sleeve 4 can enable better control of the plunger 8 and thus better application of medicine.

DESCRIPTION OF THE ALTERNATE EMBODIMENT OF FIGS. 19–20 USING A DEFORMABLE FORM BAG

A further embodiment, as shown in FIG. 19, works with a standard Playtex bottle, collar and nipple. The disposable bag itself is replaced by a specially designed, deformable plastic bag 40 that has the same characteristics at the collar/nipple end as a standard Playtex bag, as understood by those of ordinary skill in the art. However, the other end of the bag also has tabs 42 that fold over bottom of the bottle and hold fast. Additionally, there is an opening to a sleeve 44 within the bag 40 in which a syringe assembly may be inserted. The steps for assembling this embodiment include:

1. Securing collar tabs and adding liquid;
2. Evacuating excess air in bag;
3. Pulling bag up and securing the bottom tabs by pulling the bottom tabs over the bottom of the bottle;
4. Inserting the syringe for use.

In this embodiment, the tip characteristics could be made as part of the plastic bag itself and simply punctured by pressure when the plunger is depressed. Also, the tip characteristics could be built into a bushing 46 to hold the syringe. The tip 48 of the bushing 46 could also puncture the bottom seal of the plastic sleeve when inserted, thus permitting the flow of medicine from the syringe through the tip 48 and into the nipple area. Different diameter syringes could also be accommodated in this design.

Figure 20A:
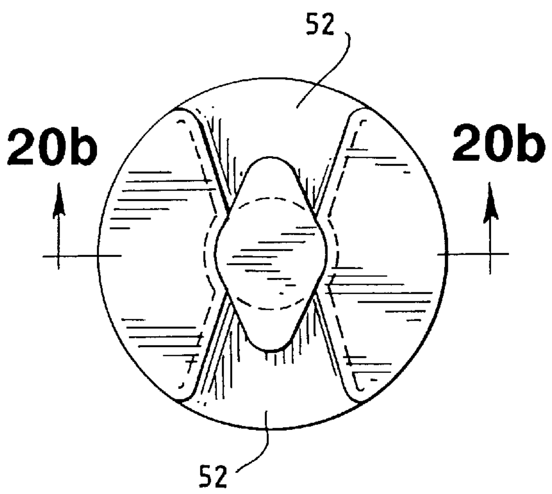
FIGS. 20*a* and 20*b* illustrate a bottom view and an exposed cross section, respectively, of a recessed bottom feature of a preferred embodiment of the present invention for easier placement and one-handed operation.
Figure 20B:
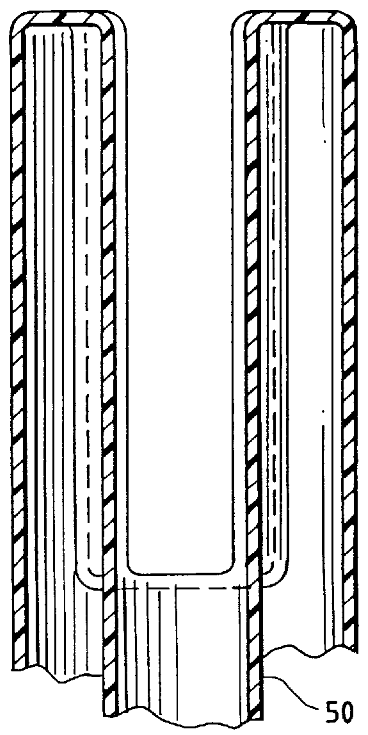

FIGS. 20*a* and 20*b* show a yet another preferred embodiment of the present invention. This embodiment includes a bottle bottom with a recessed sleeve 50 and recesses 52 for the syringe wings. This version relies on the fluid tight seal between the syringe tip and the sleeve tip to hold several commercially available syringes secure. The recess was designed into the device because it reduces the “stretch” necessary to operate the plunger and thus allows for better control of the medicine dosage and easier one-handed operation. The recess also allows for the bottle to be set down ont it’s bottom when the dosage is completed (i.e., when the plunger fully depressed).

The bottle bottom area that is not recessed is molded as an integral part of the bottle itself and so it also holds the milk or juice. This embodiment calls for two injection molded pieces that are then welded together just beyond the recess. Of course, the two pieces could also be threaded to allow for disassembly and easier cleaning.

The sleeve tip 48 of this embodiment is permanently fixed and recessed just below the bottle top. This assures there is no structure to bite or cause potential injury (with or without the nipple and collar assembly attached). The sleeve tip is restricted down to an opening of between 0.010" and 0.035" in a distance from syringe tip of approximately 0.050". This restricting tip produces it’s “jet” effect in such a short distance that it reduces the loss in the line to less than 2 drops. This feature promotes accuracy and allows for the use of currently existing syringes without the need to account for any additional loss in the line.

For a 5 ml dose (this version holds a 1, 3 & 5 ml syringe), approximately twenty quick, small squirts (pushes on the plunger) are necessary to complete the dosage. The “jet” of medicine or vitamins created by the restricted sleeve tip, the “venturi” effect created by the placement of the sleeve tip in the center of the bottle and the infant’s sucking action, along with gravity, all combine to displace the milk or juice in the very tip of the nipple. The infant sucks in the medicine and then the milk immediately thereafter, washing it down as he or she goes. If the infant appears disturbed, the operator can simply increase the time between squirts and/or use smaller squirts.

There are not additional pieces to attach, remove, loose or cause harm. The bottle, recessed sleeve and restricting tip are all provided in one piece and the device will accept any standard collar and nipple, as well as several currently available syringes. It is especially important that the infant can use the nipple they are accustomed too.

The present invention avoids any alignment problems because the device works the same no matter how the collar and nipple end up when screwed on. This feature also promotes easier operation. The device also does not effect the overall flow of combined fluids which could promote choking (especially in very young infants). The person administering the medicine completely controls the flow of medicine. The infant controls the flow of the milk or juice, as well as the overall flow into the mouth of combined fluids. Alternatively, this embodiment could also be used with a puncturing syringe if used with the pre-packaged medicine or vitamins, and the puncturing syringe could be used with or without the bottle.

This device has applications to several other groups including certain animals as well as some disabled children/adults and geriatric patients.

Figure 21A:
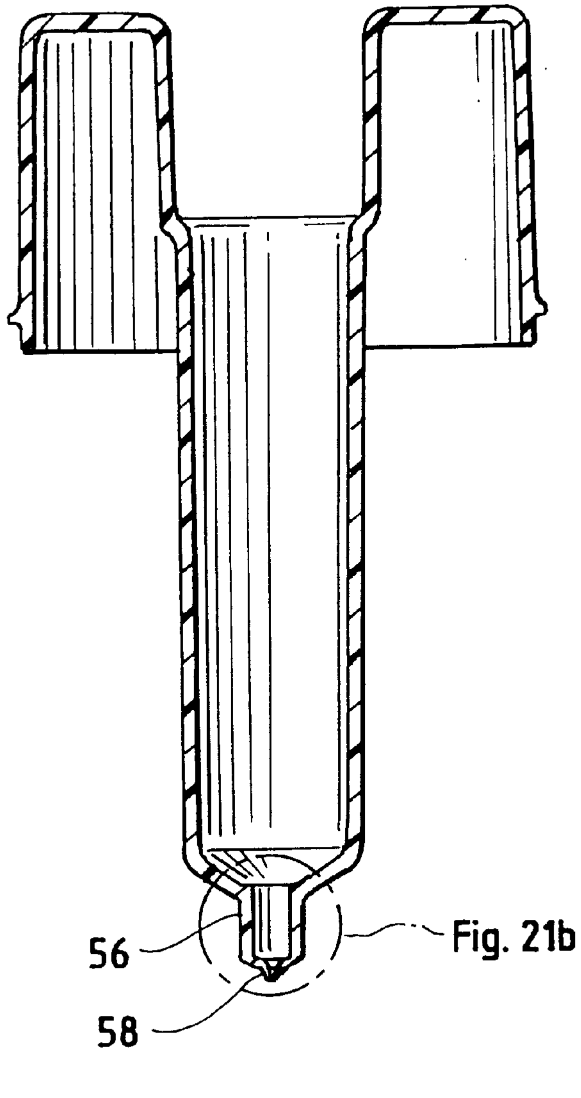
FIGS. 21*a* and 21*b* show a side cross section and a detail of the preferred restricted tip feature of a preferred embodiment of the present invention for creating a fluid jet stream and minimizing the "loss in the line" of fluid in the syringe.
Figure 21B:
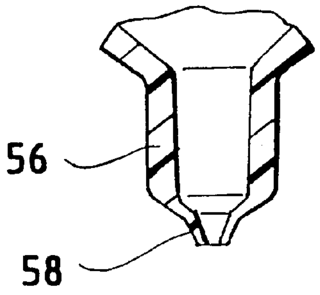
Figure 22:
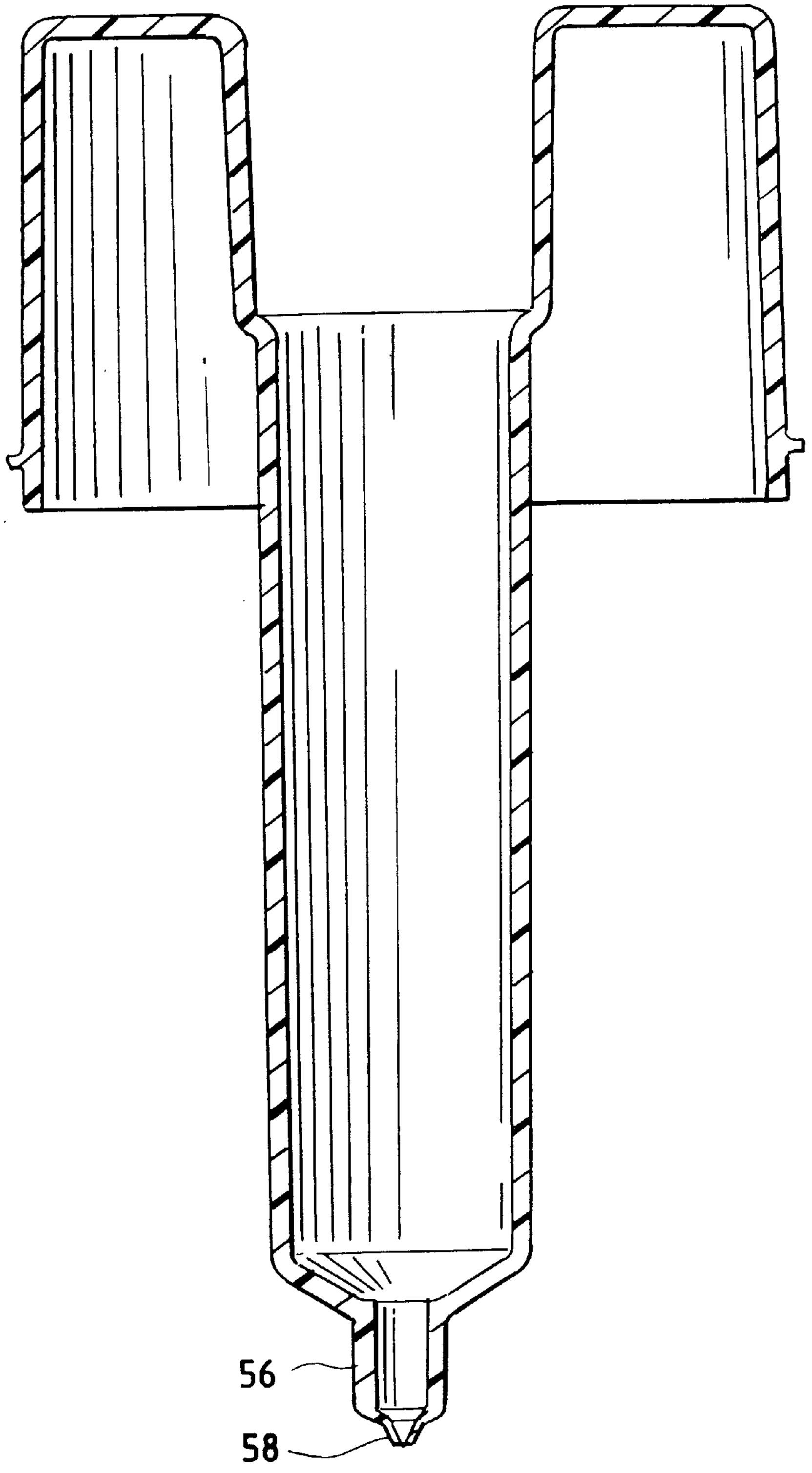
FIG. 22 shows an exposed sideview of a half molding having the restricted tip and recessed bottom features of a preferred embodiment of the present invention.

DESCRIPTION OF THE ALTERNATE EMBODIMENT OF FIGS. 21–22 USING A SPECIALLY CONFIGURED RESTRICTED TIP

The restricted tip 54 of this embodiment is integral to the internal sleeve/bottom portion of the bottle and is molded or otherwise attached to the remainder of the bottle such that the tip 54 is permanently fixed and recessed just below the bottle top. This assures there is no structure to bite or cause potential injury (with or without the nipple and collar assembly attached). The sleeve tip begins in a lower tip portion 56 that restricts the opening of the internal sleeve to an internal diameter of approximately 0.1487 inches. The lower tip portion 56 extends for a length of approximately 0.285 inches, at which point the tip further restricts to an upper tip portion 58 having an ultimate internal diameter (i.e., the diameter at the opening) of approximately 0.020 inches. The upper tip portion extends for approximately 0.082 inches. Thus, the entire restricted tip 54 in this preferred embodiment extends only for a total of 0.367 inches. This restricting tip optimizes the "jet" effect while simultaneously minimizing the loss in the line to less than 1 drop or less. This feature promotes accuracy and allows for the use of currently existing syringes without the need to account for any additional loss in the line. Further, this restricted tip embodiment eliminates the need to calculate "loss in the line" when administering dosages to infants. However, it should be understood that the optimal preferred embodiment of this configuration when applied to infants provides a restricted tip that is completely receded from the top opening or nipple area of the bottle.

It will be apparent to those of ordinary skill in the art that many changes and modifications could be made while remaining within the scope of the invention. For example, the syringe 5 and internal sleeve 4 need not be coaxial with the longitudinal axis of bottle 1. Using an appropriately curved tip member 13, it would be possible to locate the internal sleeve 4 and the syringe 5 off to one side of the center axis of the bottle 1. This alternative would permit engraving volumetric graduations on the barrel of the sleeve for viewing by the user. The curved tip member 13 would convey the liquid medication to the appropriate location inside nipple 14. A non-coaxial design may be most suitable to accommodate a syringe that has an off-center tip in the case of the above mentioned disposable embodiment.

The important point is to retain the syringe 5 inside the bottle 1, so as to avoid dangerous and clumsy radially-projecting parts such as appear in the Roskilly and Krammer references and to allow for easy one handed operation. The on-axis design of our invention allows any standard nipple or sipper top (for older children) without the user having to accommodate a specific, awkward alignment.

Alternative methods of retaining the syringe 5 inside the internal sleeve 4 could be used—pressure-sensitive adhesive on the bottom 2 of bottle 1, for example. And, of course, any palatable beverage can be used in the bottle 1, including but not limited to milk, infant formula, water, fruit juices and the like.

Figure 23:
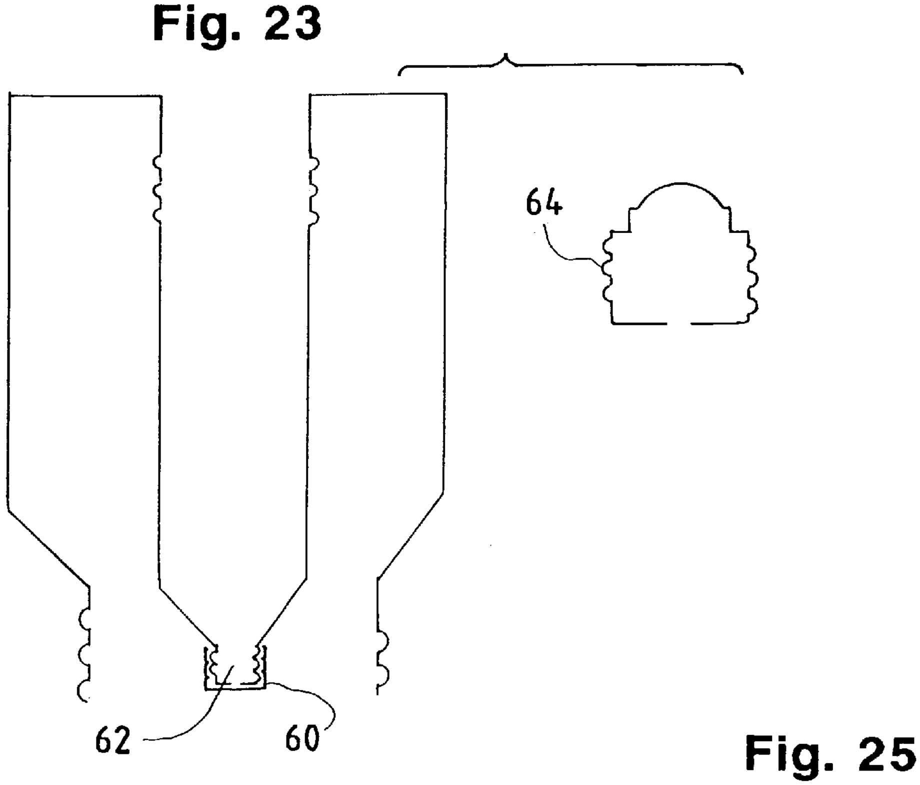
FIG. 23 shows an exposed cross-section of yet another preferred embodiment of the present invention employing a variable restrictive tip using a wing and restrictive collar arrangement and further employing an airpump screw-on plug for medicine delivery.

DESCRIPTION OF THE ALTERNATIVE EMBODIMENT OF FIGS. 23–24 USING A VARIABLE RESTRICTIVE TIP AND PUMP DELIVERY

The variable restrictive tip of this preferred embodiment is designed to accommodate a variety of different size oral dispensers, For instance, our experiments with various tip diameters has shown that a 5 mL dosage optimally has a 0.022" diameter opening, the 3 mL optimally has a 0.018" diameter opening and a 1 mL optimally has a 0.012" diameter opening.

Figure 24A:
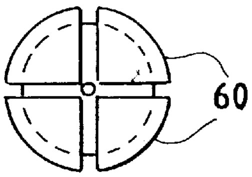
FIGS. 24*a–b* shows exposed top views of the open and closed positions for the wings feature of the variable restrictive tip embodiment of the present invention.
Figure 24B:
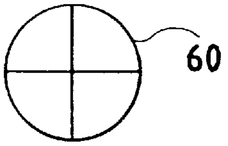

In this embodiment, the restrictive tip is comprised of a plurality of constricting wings 60 that could be opened to any diameter in the range listed above. The wings 60 can be restricted to close the tip diameter completely through the use of a constrictive collar 62, as shown in FIGS. 24*a–b*. The wings can be made of a similar material as the internal sleeve and are preferably integral to and extending along the length of the internal sleeve. The restrictive collar would be connected to the wings on the internal sleeve by a threaded engagement, and would be alternatively opened or closed by clockwise or counterclockwise rotation.

Alternatively, the variable restrictive tip feature of this embodiment could be accomplished by push-pull configuration between the tip area and the restrictive collar 62, similar to openings found currently in squeezable water bottles. In such an arrangement, the restrictive collar could have a number of detents or stops along the length of the tip area in order to accommodate openings of preselected diameters in the range defined above.

Figure 25:
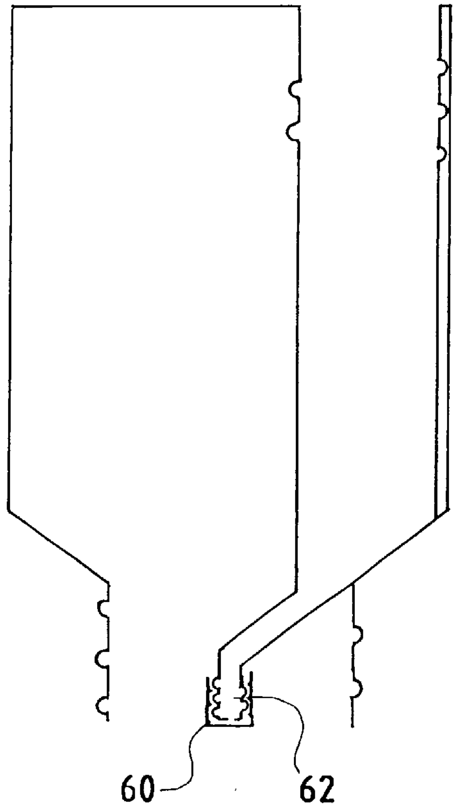
FIG. 25 shows another alternative embodiment of the airpump plug feature of the present invention having an offset internal sleeve.

Another feature of this alternative embodiment is the use of a screw-in plug 64 with an airpump. This pump feature of this alternative embodiment would avoid the need for a plunger or similar mechanical interface with the medicine in the internal sleeve. In this embodiment, the plug could be aligned with an internal sleeve that was not co-axial with the bottle, nor would it even need to be placed on the bottom of the bottle. One advantage of moving the internal sleeve towards the side of the bottle would be the accommodation of graduations along the side of the bottle, thus facilitating easier monitoring of the volume of medicine delivered. As shown in FIG. 25, the plug 64 would preferably be placed in the recessed bottom of the bottle and would be seated in the recessed bottom using a threaded or detent arrangement. Alternatively, this plug placement could be accommodated along the sides of the bottle.

In order to administer medicine using the alternative plug design, the user would first have to shut off the tip area. Then the user would have to measure out the prescribed dose and pour that dose into the sleeve. Next, the user would have to either screw or snap on the airpump plug, priming the internal sleeve by pressing the pump until medicine was forced up to the tip area. Once the internal sleeve is primed, the user could then fill the bottle with milk or other palatable liquid.

It is important to note that the airpump plug could function with or without an adjustable tip, because the sleeve diameter to which the pump is attached is constant. Thus, dosages of different volumes would be delivered in the same way. This alternative embodiment is further advantageous because the person administering the medicine would not need to stretch his or her hand beyond the length of the bottle, since the plug is preferably recessed in the bottom.

DESCRIPTION OF AN ALTERNATIVE EMBODIMENT FOR ACCOMMODATING VISCOUS MEDICINES

A further preferred embodiment of our invention is designed to accommodate medicines having high viscosities. Our tests of other preferred embodiments have shown that certain medicines such as acetaminophen in a sugar solution (e.g., childrens' "suspension" Tylenol®) or clarithromycin (Biaxin) tend to occlude the tip area and/or fail to create the necessary jetstream of medicine into the nipple area of the bottle. For such medicines, our preferred embodiment would include a sleeve tip diameter up to 0.1251". However, this increased sleeve tip diameter necessitates extending the sleeve tip further towards the nipple area than in other preferred embodiments. Ideally, this preferred embodiment would include an extended tip from about 0.5" to 0.06" from the nipple port. Although the extended tip of this embodiment may be sensed through the nipple by the child or other recipient, and the length of the tip area requires purging in order to avoid a loss of medicine in the tip area, this configuration will allow for a successful delivery and mixture with the milk or other liquid.

Alternatively, the use of a soft extension or bushing to the sleeve tip configuration, as disclosed in other embodiments of this invention, would allow for a 1 mL syringe to accommodate viscous medicines. The purpose of the extension is not necessarily because of "thick" medicine, but because a 1 mL dispenser barrel is so small in diameter. The need to restrict flow increases, which also allows for less medications to pass through.

Another reason to add an extended tip (with or without a restricted sleeve tip further back) is to reduce manufacturing costs or eliminate backpressure and the need to jet medication at all. In the first case, an extended tip would improve the aim of the "jet stream" of medicine into the nipple. This extended tip could also be used to accommodate an off-center delivery (e.g., into a "sipper top" with offset sipping ports for older children). The medicine would contact whatever initial internal sleeve tip wall it hit first with great force. Using this extended tip would not create any "loss in line" problem as long as the extended tip is restricted near the internal sleeve tip termination point.

As with the other embodiments of this invention, it should be understood that the present invention could have any number of configurations that could utilize non conventional shape, such as a "bottle nose" dolphin, with the nipple area being placed within the "nose" of the dolphin. In such an alternative embodiment, the "bottle" (i.e., the container or dolphin shape) might have an atypical proximal or bottom end in that might not have a substantially flat bottom surface for resting the bottle. This alternative embodiment, however, like other alternative embodiments of this invention, would have benefits over the prior art in that the syringe sleeve opening that is proximal from the distal, nipple area of the "bottle," and yet is integral to the "bottle" form. Most preferably, this alternative embodiment would have a axial internal syringe sleeve extending from the proximal end (i.e., the bottom or "tail" of the dolphin) towards, yet separate from the nipple area at the top opening.

Of course, it should be understood the changes or additional can be made without deviating from the scope or spirit of these or other embodiments. It is our intention to cover all such equivalent structures, and to limit our invention only as specifically delineated in the following claims.

We claim:

1. A liquid medication dispenser suitable for delivering a controllable mixture of a palatable beverage into which a liquid medication has been diluted, comprising:

a. a container having a proximal end and a distal end, said distal end having a top opening;

b. a nipple attached to said top opening and having one or more perforations therein to allow liquid to pass through;

c. a internal sleeve extending longitudinally from said proximal end of said container axially in the direction of said top opening, and having an open proximal end and a distal end, said distal end of said sleeve being longitudinally separated from said nipple;

d. a removable syringe operatively attached into said internal sleeve, said syringe having a distal end and a proximal end, said proximal end being provided with a plunger, said distal end of said syringe being longitudinally separated from said nipple;

e. a variable tip formed on the distal end of said internal sleeve and extending a predetermined distance towards the perforation in said nipple, said tip having a lower tip portion and an upper tip portion, said variable tip including adjustable flow means for facilitating a plurality of aperture diameters for said distal end of said internal sleeve.

2. The liquid medication dispenser of claim 1, wherein said adjustable flow means comprises a restrictive collar, said collar having a threaded engagement with the distal end of said internal sleeve.

3. The liquid medication dispenser of claim 2, wherein the threaded engagement of said restrictive collar includes a plurality of detents to facilitate a variety of preselected tip aperture diameters.

* * * * *